(12) United States Patent
Matsuo et al.

(10) Patent No.: US 9,468,361 B2
(45) Date of Patent: Oct. 18, 2016

(54) ENDOSCOPE

(71) Applicant: OLYMPUS CORPORATION, Tokyo (JP)

(72) Inventors: Shigeki Matsuo, Kokubunji (JP); Yasushi Machida, Hachioji (JP)

(73) Assignee: OLYMPUS CORPORATION (JP)

( * ) Notice: Subject to any disclaimer, the term of this patent is extended or adjusted under 35 U.S.C. 154(b) by 533 days.

(21) Appl. No.: 13/947,673

(22) Filed: Jul. 22, 2013

(65) Prior Publication Data

US 2013/0303854 A1 Nov. 14, 2013

Related U.S. Application Data

(63) Continuation of application No. 12/335,003, filed on Dec. 15, 2008, now abandoned.

(30) Foreign Application Priority Data

Dec. 26, 2007 (JP) ................................. 2007-335325

(51) Int. Cl.
| | | |
|---|---|---|
| *A61B 1/00* | (2006.01) | |
| *A61B 1/04* | (2006.01) | |
| *A61M 25/00* | (2006.01) | |
| *F16L 11/00* | (2006.01) | |
| *F16L 9/22* | (2006.01) | |
| *A61B 1/005* | (2006.01) | |
| *G02B 23/24* | (2006.01) | |

(52) U.S. Cl.
CPC ............. *A61B 1/005* (2013.01); *A61B 1/0055* (2013.01); *G02B 23/2476* (2013.01)

(58) Field of Classification Search
USPC ......... 600/127–130, 139–152; 138/118–153, 138/155; 604/523–528
See application file for complete search history.

(56) References Cited

U.S. PATENT DOCUMENTS

| | | | |
|---|---|---|---|
| 4,841,952 A | 6/1989 | Sato | 600/129 |
| 5,275,152 A | 1/1994 | Krauter | 600/129 |
| 6,083,152 A | 7/2000 | Strong | 600/139 |
| 6,485,411 B1 | 11/2002 | Konstorum | 600/139 |
| 2001/0023313 A1* | 9/2001 | Ide | 600/142 |
| 2006/0258911 A1* | 11/2006 | Sato | A61B 1/00071 600/139 |
| 2007/0233040 A1* | 10/2007 | Macnamara | A61B 1/00071 604/523 |

FOREIGN PATENT DOCUMENTS

| | | | |
|---|---|---|---|
| JP | 2002-034899 | 2/2002 | |
| JP | 2004-329857 | 11/2004 | |
| JP | 2004329857 A | * 11/2004 | ............... A61B 1/00 |

OTHER PUBLICATIONS

Search Report issued by European Patent Office and received by applicant on Dec. 7, 2012 in connection with corresponding EP patent application No. EP 08 021 816.7.

* cited by examiner

*Primary Examiner* — Ryan Henderson
(74) *Attorney, Agent, or Firm* — Ostrolenk Faber LLP

(57) ABSTRACT

An endoscope includes a flexible tube and a connection mouth ring. The flexible tube includes a helical tube, a braid tube disposed outside the helical tube, and an outer tube disposed outside the braid tube. The endoscope further includes a caulking member which caulks the end of the braid tube from the outside of the connection mouth ring in a state held therebetween. The end of the helical tube is connected by thermal action to the connection mouth ring, and a part where the end of the helical tube is connected to the connection mouth ring is positioned differently along the axis of the connection mouth ring from a part where the end of the braid tube is caulked against the connection mouth ring.

6 Claims, 8 Drawing Sheets

ENDOSCOPE

CROSS-REFERENCE TO RELATED APPLICATIONS

The present application is a continuation under 37 C.F.R. §1.53(b) of prior application Ser. No. 12/335,003, filed Dec. 15, 2008, by Shigeki MATSUO et al., entitled ENDOSCOPE, which is based upon and claims the benefit of priority from prior Japanese Patent Application No. 2007-335325, filed Dec. 26, 2007, the entire contents of which are incorporated herein by reference.

BACKGROUND OF THE INVENTION

1. Field of the Invention

This invention relates to an endoscope used for various purposes such as an industrial purpose and a medical purpose.

2. Description of the Related Art

An endoscopic flexible tube is formed by stacking a helical tube, a braid tube (mesh tube) and a flexible outer tube in order from the inside to the outside. Then, the distal end of the flexible tube is connected to the proximal end of a bending portion by a connection mouth ring.

For example, at the distal ends of the helical tube and the braid tube, a hard portion is formed in which these tubes are joined, for example, by an adhesive or by brazing (soldering or brazing). Further, a mouth ring member is fixed to the outside of the hard portion of the helical tube and the braid tube.

BRIEF SUMMARY OF THE INVENTION

An endoscope according to this invention includes: a flexible tube having a helical tube, a braid tube disposed outside the helical tube, and a flexible outer tube disposed outside the braid tube; a cylindrical connection mouth ring connected to an end of the flexible tube; and a caulking member by which an end of the braid tube is caulked outside the connection mouth ring in a state held therebetween. An end of the helical tube is connected by thermal action to the connection mouth ring inside the braid tube, and a part where the end of the helical tube is connected to the connection mouth ring is positioned differently along the axis of the connection mouth ring from a part where the end of the braid tube is caulked against the connection mouth ring by the caulking member.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, a best mode for carrying out this invention will be described with reference to the drawings.

First Embodiment

A first embodiment is described with FIG. 1 to FIG. 7.

Figure 1:
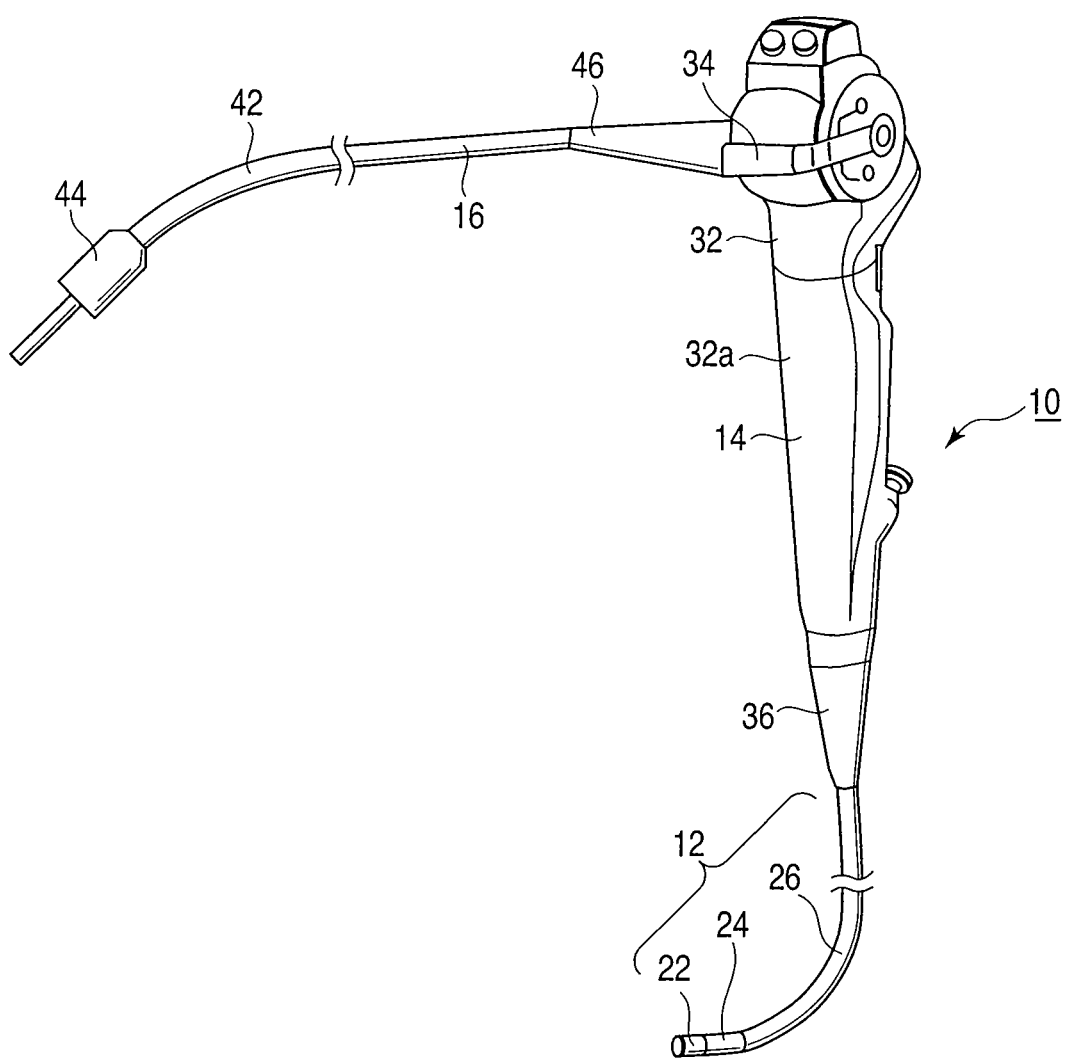
FIG. 1 is a schematic view showing an endoscope according to first to third embodiments.
Figure 2:
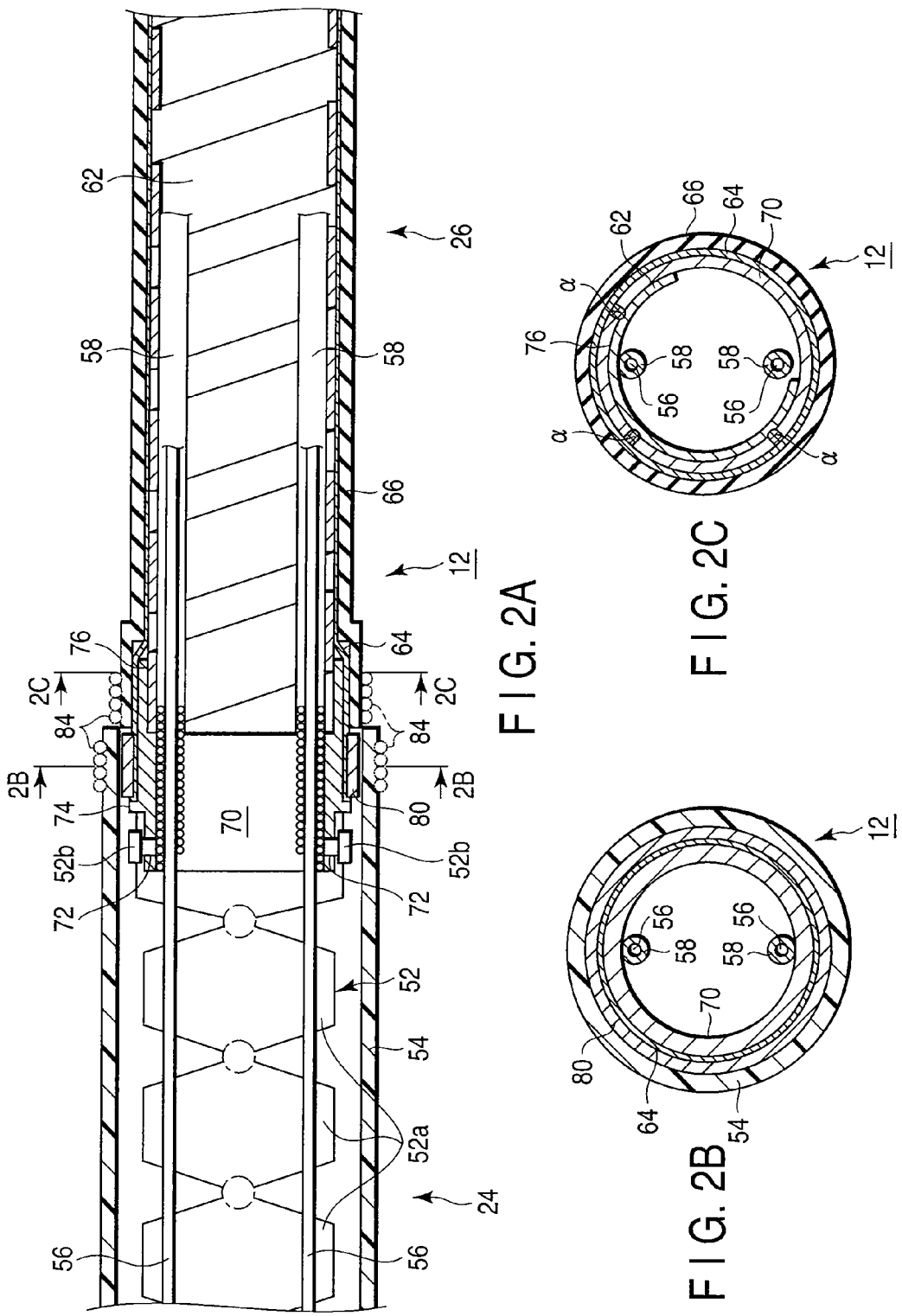
FIG. 2A is a schematic longitudinal sectional view showing a bending portion, a flexible tube and a connection mouth ring for connecting the bending portion to the flexible tube of an insertion portion in the endoscope according to the first embodiment.
FIG. 2B is a schematic cross sectional view of the insertion portion along line 2B-2B in FIG. 2A.
FIG. 2C is a schematic cross sectional view of the insertion portion along line 2C-2C in FIG. 2A.

As shown in FIG. 1, an endoscope 10 includes an insertion portion 12 to be inserted into a narrow and small space, an operation portion 14 disposed at the proximal end of the insertion portion 12, and a universal cable 16 extending from the operation portion 14.

The insertion portion 12 includes a distal hard portion 22, a bending portion 24 disposed at the proximal end of the distal hard portion 22, and a flexible tube 26 disposed at the proximal end of the bending portion 24. The operation portion 14 includes an operation portion main body 32 with a grip portion 32a, a bending operation knob 34 disposed in the operation portion main body 32, and a protection hood 36 disposed at the proximal end of the flexible tube 26 and disposed in the grip portion 32*a* of the operation portion main body 32. The universal cable 16 includes a flexible tube 42 extending from the operation portion main body 32, and a connector 44 disposed at the end of the flexible tube 42 on the distal side with respect to the operation portion main body 32. A protection hood 46 is disposed between the flexible tube 42 of the universal cable 16 and the operation portion main body 32.

As shown in FIG. 2A, the bending portion 24 of the insertion portion 12 includes a bending tube 52 which is bent by the operation of the operation portion 14, and a cover tube 54 disposed outside the bending tube 52. The bending tube 52 is formed by joining a plurality of bending pieces 52*a* axially rotatably with respect to each other. For example, a pair of operation wires 56 is inserted into each of the bending pieces 52*a*. These operation wires 56 have their proximal ends fixed to the bending operation knob 34 of the operation portion 14, and their distal ends fixed to the most distal bending piece 52*a* of the bending tube 52 or to the distal hard portion 22. That is, the operation wires 56 are inserted in the bending portion 24 and the flexible tube 26 of the insertion portion 12.

In addition, each of the operation wires 56 is covered with a cover coil 58. The distal end of the cover coil 58 is fixed to the inner peripheral surface of a connection mouth ring 70 described later by, for example, adhesive bonding or brazing (soldering or brazing). The cover coil 58 is disposed to extend up to the proximal side of the flexible tube 26.

The flexible tube 26 includes a helical tube (spiral tube) 62, a braid tube (mesh tube) 64 disposed outside the helical tube 62, and a flexible outer tube 66 disposed outside the braid tube 64.

The helical tube 62 is formed by helically molding a thin strip plate material made of, for example, stainless steel into the shape of a substantially circular tube. The thin plate material of the helical tube 62 is, for example, about 3 mm in breadth. The distal end of the helical tube 62 is cut so that it is about 90 degrees (including 90 degrees) to the longitudinal central axis of the helical tube 62.

Figure 3:
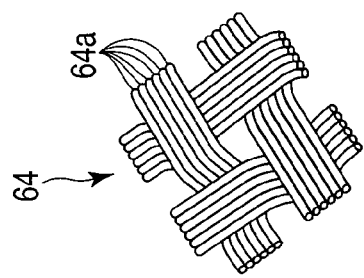
FIG. 3 is a schematic perspective view showing a part of a braid tube used for the insertion portion or a universal cable of the endoscope according to the first to third embodiments.

As shown in FIG. 3, in the braid tube 64, bundles of a plurality of knitted strands 64*a* made of, for example, stainless steel are formed into the shape of a substantially circular tube. The strands cross each other in the braid tube 64, so that this thickness of the braid tube 64 corresponds to the addition of the outside diameters of two strands 64*a*.

The outer tube 66 is formed of a flexible resin material such as a rubber material into the shape of a substantially circular tube so that it covers the outside of the braid tube 64.

Furthermore, the proximal end of the bending tube 52 of the bending portion 24 is connected to the distal end of the flexible tube 26 via the connection mouth ring 70.

As shown in FIGS. 2A to 2C, the connection mouth ring 70 is formed of, for example, a metal such as stainless steel into a substantially cylindrical shape. At the distal end of the connection mouth ring 70, for example, a pair of opposite openings 72 is formed so that connecting pins (or connecting screws) 52*b* for connecting to the most proximal bending piece 52*a* of the bending tube 52 penetrates and is thus disposed in the openings. A diametrically outwardly projecting flange portion 74 is formed on the proximal side of the part of the connection mouth ring 70 where the openings 72 are formed. On the inner peripheral surface of the proximal end of the connection mouth ring 70, there is formed a concave portion 76 having an inside diameter formed to be larger than the distal end of the connection mouth ring 70.

The inner peripheral surface of the connection mouth ring 70 forms a uniform surface from its distal end to the distal end of the concave portion 76. The concave portion 76 of the connection mouth ring 70 is formed to have an inside diameter larger than the inside diameter from the distal end of the connection mouth ring 70 to the distal end of the concave portion 76. The outer peripheral surface of the connection mouth ring 70 is formed so that the thickness from its distal end to the flange portion 74 is smaller than the thickness of the outer peripheral surface from the flange portion 74 to the position where the concave portion 76 is formed. The outer peripheral surface of the connection mouth ring 70 forms a uniform surface from the flange portion 74 to the proximal end. That is, the connection mouth ring 70 is formed to have the largest thickness at the position from the flange portion 74 to the distal end of the concave portion 76 along the axis of the connection mouth ring 70.

The thickness of the connection mouth ring 70 from its distal end to the flange portion 74 is suitably formed to consider the size of the head of the connecting pin 52*b* disposed in the pair of openings 72 from the outside of the connection mouth ring 70. Specifically, the tops of the heads of the connecting pins 52*b* disposed in the openings 72 of the connection mouth ring 70 are suitably positioned as high as or lower than the top of the flange portion 74.

The inside diameter of the concave portion 76 of the connection mouth ring 70 is formed to be equal to or smaller than the outside diameter of the helical tube 62 so that the outer peripheral surface of the helical tube 62 may be in close contact with the inner peripheral surface of the concave portion 76 when the single helical tube 62 is placed in a natural state (state of no external force applied). The distal end of the helical tube 62 is cut at about 90 degrees to its axis. Thus, the outer peripheral surface of the helical tube 62 is urged against the inner peripheral surface of the concave portion 76 of the connection mouth ring 70, and at the same time, the distal end of the helical tube 62 is in contact with a step portion of the distal end of the concave portion 76. That is, the distal end of the helical tube 62 is fitted in a positioned state in the concave portion 76 of the connection mouth ring 70.

As shown in FIGS. 2A and 2C, while the connection mouth ring 70 and the helical tube 62 are in a fitted state as described above, a place (its width has only to be, for example, about 1 mm along the axis) where the connection mouth ring 70 and the helical tube 62 overlap each other is only spot-welded by laser from the outside of the connection mouth ring 70 at proper intervals or repeatedly, such that welded portions α welded at predetermined intervals or welded in a continuous circumferential (arc-like) shape (see FIG. 2C) are formed. That is, the welded portions α are formed in the connection mouth ring 70 circumferentially or along the helical of the helical tube 62. This makes it possible to connect the helical tube 62 to the connection mouth ring 70 without increasing the connection part axially. At this point, the connection mouth ring 70 is instantaneously heated in the laser welding, so that the transmission of heat from the connection mouth ring 70 to the outer tube 66 is prevented to the maximum even if the welding takes place in the vicinity of the outer tube 66.

In addition, the inside diameter of the concave portion 76 of the connection mouth ring 70 is formed to be smaller than the outside diameter of the distal end of the helical tube 62, so that the fitting state of the connection mouth ring 70 and the helical tube 62 can be easily maintained, and the formation of a gap therebetween is prevented. Moreover, the distal end of the helical tube 62 is cut at about 90 degrees to its axis, and the distal end of the helical tube 62 is positioned at the distal end of the concave portion 76 of the connection mouth ring 70. Thus, there is no need to weld axially relative to the connection mouth ring 70, and welding strength is also easily assured by circumferentially welding in an arc-shaped manner (or welding along the helical shape of the helical tube 62), thereby highly contributing to the reduction of the axial length of the connection mouth ring 70 (the reduction of the axial length of the hard portion).

Although carrying out the laser spot welding to fix the helical tube 62 to the connection mouth ring 70 has been described here, brazing, for example, in the helical direction of the strip plate of the helical tube 62 may be carried out instead of the laser spot welding. That is, it is only necessary that the helical tube 62 be fixed to the connection mouth ring 70 by proper thermal action so that the effect of the helical tube 62 axially relative to the connection mouth ring 70 may be minimized.

Furthermore, as shown in FIGS. 2A and 2B, the distal end of the braid tube 64 is disposed on the proximal side of the flange portion 74 of the connection mouth ring 70 and outside the connection mouth ring 70. Further, a caulking member 80 is disposed outside the braid tube 64. The caulking member 80 is formed of, for example, a metal such as stainless steel so that its axial width is about 2 mm. In addition, although the caulking member 80 shown in FIG. 2B is ring-shaped, the caulking member 80 may be, for example, C-shaped instead. Thus, various kinds of caulking members 80 are used.

The caulking member 80 is positioned substantially in contact with the flange portion 74 of the connection mouth ring 70. That is, the flange portion 74 of the connection mouth ring 70 functions as a positioning portion of the caulking member 80. Since the caulking member 80 is fixed to the connection mouth ring 70 so that it is positioned with respect to the positioning portion as described later, the braid tube 64 can be easily caulked against the connection mouth ring 70 in such a manner as to prevent displacement.

Here, while the axial length of the caulking member 80 can be properly set, the proximal end of the caulking member 80 is suitably at the same position as the outer periphery of the distal end of the concave portion 76 of the connection mouth ring 70 or at a position closer to the distal side. Therefore, if the caulking member 80 is about 2 mm as described above, the length of the connection mouth ring 70 between the proximal end surface of the flange portion 74 of the connection mouth ring 70 and the distal end of the concave portion 76 has only to be formed to be slightly larger. When the caulking member 80 is caulked (plastically deformed) against the outside of the connection mouth ring 70, the caulking member 80 is caulked in a state positioned with respect to the connection mouth ring 70, and the braid tube 64 is held and fixed between the outside of the connection mouth ring 70 and the inside of the caulking member 80.

In addition, when the caulking member 80 is caulked against the outside of the connection mouth ring 70, a part of the caulking member 80 that has been caulked (hereinafter referred to as a caulked part) is displaced with respect to the welded portions α axially relative to the connection mouth ring 70. This can prevent stress by which the caulking member 80 is caulked from being directly applied to the welded portions α outside the connection mouth ring 70 where the distal end of the helical tube 62 is welded to the concave portion 76 of the connection mouth ring 70. That is, the welded portions α can be prevented from being damaged by the caulking of the caulking member 80 with respect to the connection mouth ring 70. Thus, even if the caulking member 80 is caulked against the outside of the connection mouth ring 70, the strength of the welding that fixes the connection mouth ring 70 and the helical tube 62 together can be maintained. Moreover, at this point, the caulked part of the caulking member 80 is located closer to the distal side of the connection mouth ring 70 than the welded portions α and closer to the proximal side than the openings 72 and the flange portion 74. Therefore, the thickness of a substantially central portion can be greater along the axis of the connection mouth ring 70, such that the strength of the connection mouth ring 70 can be maintained. That is, the caulked part where the caulking member 80 is caulked is displaced closer to the distal side of the connection mouth ring 70 than the welded portions α where the helical tube 62 is welded in order to increase the thickness of the caulked part of the caulking member 80, such that the caulking member 80 can be more firmly caulked against the connection mouth ring 70. At this point, there is no need to apply heat to the caulking member 80 when the caulking member 80 is caulked against the connection mouth ring 70, and effects of the heat on the outer tube 66 exerted on the resin material can be prevented. Thus, even if the caulking member 80 is caulked while the caulking member 80 is in contact with the distal end of the outer tube 66, it is possible to prevent, for example, deformation of the outer tube 66 due to the effects of heat.

Figure 4:
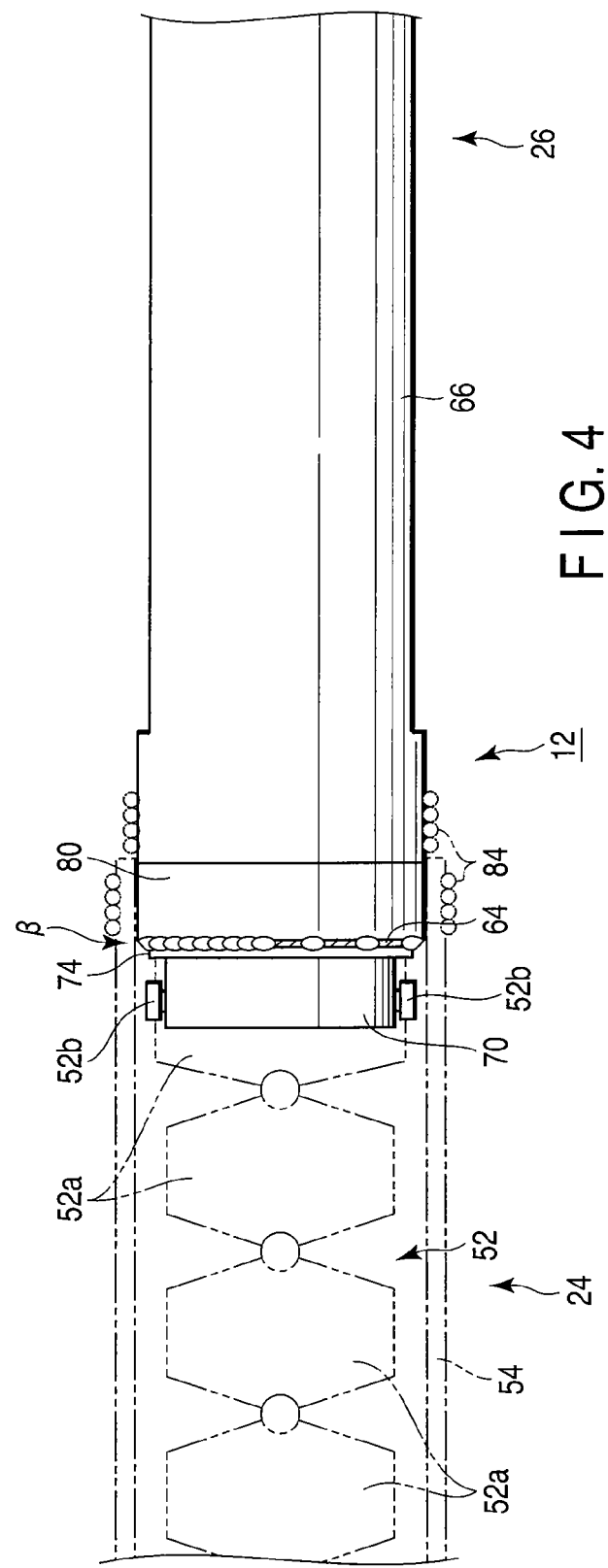
FIG. 4 is a schematic partial longitudinal sectional view showing the bending portion, the flexible tube and the connection mouth ring for connecting the bending portion to the flexible tube of the insertion portion in the endoscope according to the first embodiment.

Furthermore, as shown in FIG. 4, a weld-processed portion β which has been welded by laser is formed between the flange portion 74 of the connection mouth ring 70 and the distal end of the caulking member 80. Owing to the weld-processed portion β which has been welded in such a manner, it is possible to remove part of the braid tube 64 projecting from the distal end of the caulking member 80 and covering the flange portion 74 of the connection mouth ring 70 and the openings 72, and it is also possible to process the distal end face of the braid tube 64. Thus, the end of the braid tube 64 can be prevented from rising outward on the distal side of the flange portion 74 of the connection mouth ring 70 to, for example, rub against and scratch on the outer tube 66 or the cover tube 54.

Then, while the bending tube 52 of the bending portion 24 and the flexible tube 26 are thus fixed to the connection mouth ring 70, the cover tube 54 of the bending portion 24 covers from the outside. The proximal end of the cover tube 54 is wound with a thread 84 from the outside of the cover tube 54 so that the caulking member 80 is pressed in a diametrically inward direction of the connection mouth ring 70. The thread 84 is wound, with no space, not only around the proximal end of the cover tube 54 of the bending portion 24 but also around the distal end of the outer tube 66 of the flexible tube 26. An unshown adhesive is then applied to the thread 84 to provide watertightness between the proximal end of the cover tube 54 of the bending portion 24, the distal end of the outer tube 66 of the flexible tube 26 and the connection mouth ring 70. At this point, the caulking member 80 is disposed inside the cover tube 54 and can therefore be insulated from the outside of the insertion portion 12. Moreover, the caulking member 80 and the connection mouth ring 70 are disposed in a layer under the part which is wound with the thread 84 and to which the adhesive is applied, so that this part (the layer under the part to which the adhesive is applied) is not bent. Thus, the adhesively bonded part in which the adhesive is applied to the thread 84 is prevented from cracking.

Next, a method of attaching the connection mouth ring 70 to the flexible tube 26 and attaching the bending tube 52 of the bending portion 24 to the connection mouth ring 70 is illustrated.

Figure 5A:
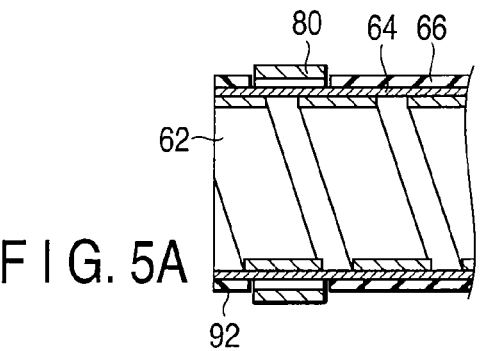
FIGS. 5A to 5G are schematic longitudinal sectional views sequentially showing the procedure of connecting the flexible tube of the insertion portion of the endoscope according to the first embodiment to the connection mouth ring.

As shown in FIG. 5A, a tape 92 is affixed to the outside of the distal ends of the helical tube 62 and the braid tube 64 to prevent the unraveling of the braid tube 64. Then, the caulking member 80 is disposed outside the helical tube 62 and the braid tube 64. At this point, the tape 92 is exposed from the distal end of the caulking member 80. In this state, the distal end of the braid tube 64 is cut to make the distal ends of the helical tube 62 and the braid tube 64 uniform so that the distal end of the helical tube 62 may be at about 90 degrees to the longitudinal direction. In addition, the tape 92 has only to be placed, for example, about 2 mm to 3 mm.

Figure 5E:
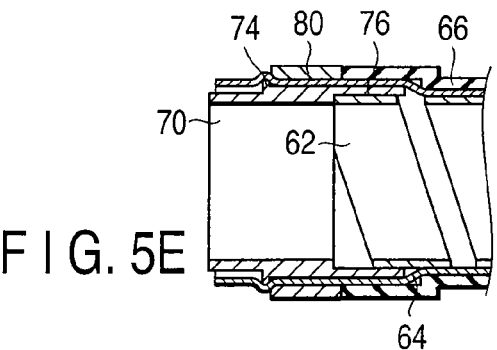
Figure 5B:
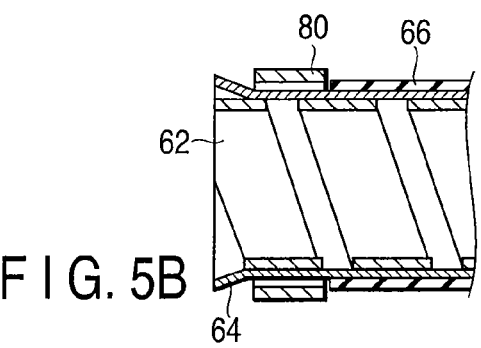

As shown in FIG. 5B, the tape 92 is removed, and the distal end of the braid tube 64 is diametrically outwardly opened.

Figure 5F:
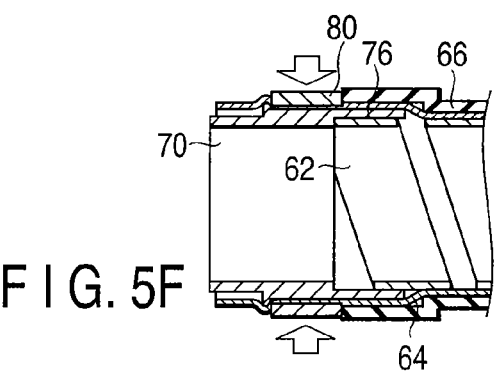
Figure 5C:
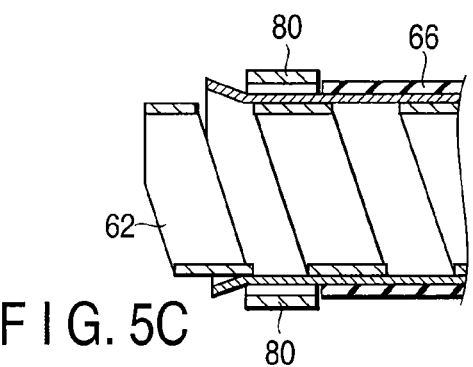

As shown in FIG. 5C, the distal end of the helical tube 62 is drawn out with respect to the distal end of the braid tube 64. At this point, the inside and outside diameters of the helical tube 62 are once reduced to draw out the helical tube 62.

Figure 5G:
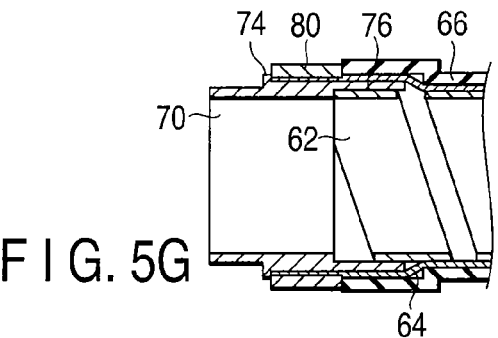
Figure 5D:
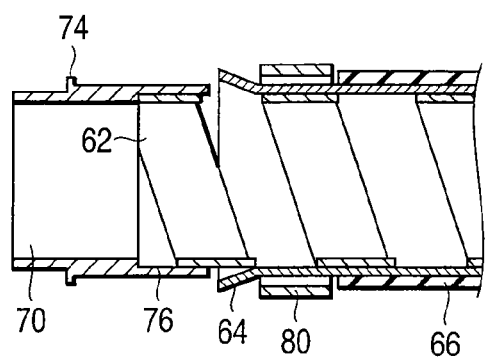

As shown in FIG. 5D, the distal end of the braid tube 64 is brought into contact with the end of the concave portion 76 of the connection mouth ring 70 to fit the helical tube 62 into the connection mouth ring 70. At this point, the outer peripheral surface of the helical tube 62 is brought into close contact with the inner peripheral surface of the connection mouth ring 70 by the diametrically outward urging force of the helical tube 62 itself. While the connection mouth ring 70 and the helical tube 62 are thus in a fitted state, the helical tube 62 and the connection mouth ring 70 are welded together by laser in a spotted manner from the outside of the connection mouth ring 70. At this point, a part where the helical tube 62 and the connection mouth ring 70 overlap each other is welded by laser in an arc-like (continuous) shape or at a plurality of places, such that the helical tube 62 and the connection mouth ring 70 are firmly fixed together.

As shown in FIG. 5E, the connection mouth ring 70 to which the helical tube 62 is fixed is pressed into the braid tube 64. Then, the distal end of the caulking member 80 is brought into contact with the flange portion 74 of the connection mouth ring 70. At this point, the distal end of the braid tube 64 is located on the distal side of the connection mouth ring 70 beyond the flange portion 74 of the connection mouth ring 70.

In addition, as described above, the thickness (see FIG. 3) of the braid tube 64 is the addition of the outside diameters of two strands 64a. Therefore, the inside diameter of the caulking member 80 before the caulking member 80 is caulked is greater than the addition of the thickness of two braid tubes 64 to the outside diameter of the connection mouth ring 70 (the addition of the outside diameters of four strands 64a of the braid tubes 64 because the braid tube 64 is cylindrical).

The caulking member 80 is caulked against the connection mouth ring 70 as shown in FIG. 5F while a core bar (not shown) for preventing the deformation of the connection mouth ring 70 and the helical tube 62 is disposed inside the connection mouth ring 70 and the helical tube 62. Thus, the caulking member 80 is positioned with respect to the flange portion 74 of the connection mouth ring 70, and at the same time, the braid tube 64 is fixed in a state held between the inside of the caulking member 80 and the outside of the connection mouth ring 70. Then, the core bar is removed from within the connection mouth ring 70 and the helical tube 62.

In addition, the outside diameter of the caulking member 80 after the caulking member 80 has been caulked is smaller than the addition of the thickness of two braid tubes 64 and the thickness of two caulking members 80 to the outside diameter of the connection mouth ring 70. Moreover, the outside diameter of the flange portion 74 for positioning the caulking member 80 is greater than the subtraction of the thickness of two braid tubes 64 from the inside diameter of the caulking member 80 before the caulking member 80 is caulked.

For example, the flange portion 74 of the connection mouth ring 70 and the distal end of the caulking member 80 are laser-welded together to form the weld-processed portion β. At this point, as shown in FIG. 5G, the distal end of the braid tube 64 is cut by, for example, a laser or a cutter at the position of the flange portion 74 and removed, and the end of the braid tube 64, the end of the caulking member 80 and the flange portion 74 of the connection mouth ring 70 are fixed by laser welding. Such processing enables the cutting of the braid tube 64 and the processing of the end face in one operation. This processing can also prevent the end of the braid tube 64 from rising outward on the distal side of the flange portion 74 of the connection mouth ring 70 to, for example, scratch on the outer tube 66 or the cover tube 54.

Then, as shown in FIG. 2A, the connecting pins 52b are disposed in the openings 72 at the distal end of the connection mouth ring 70 to connect the connection mouth ring 70 and the bending tube 52 of the bending portion 24 together. Then, the cover tube 54 is disposed outside the bending tube 52. At this point, the proximal end of the cover tube 54 covers up to the proximal end of the caulking member 80. Subsequently, the thread 84 is wound around the proximal end of the cover tube 54 and the distal end of the outer tube 66. Then, the adhesive is applied to the part wound with the thread 84 to provide watertightness between the bending portion 24, the flexible tube 26 and the connection mouth ring 70.

Thus, the bending portion 24 and the flexible tube 26 of the insertion portion 12 of the endoscope 10 are connected together.

Figure 6A:
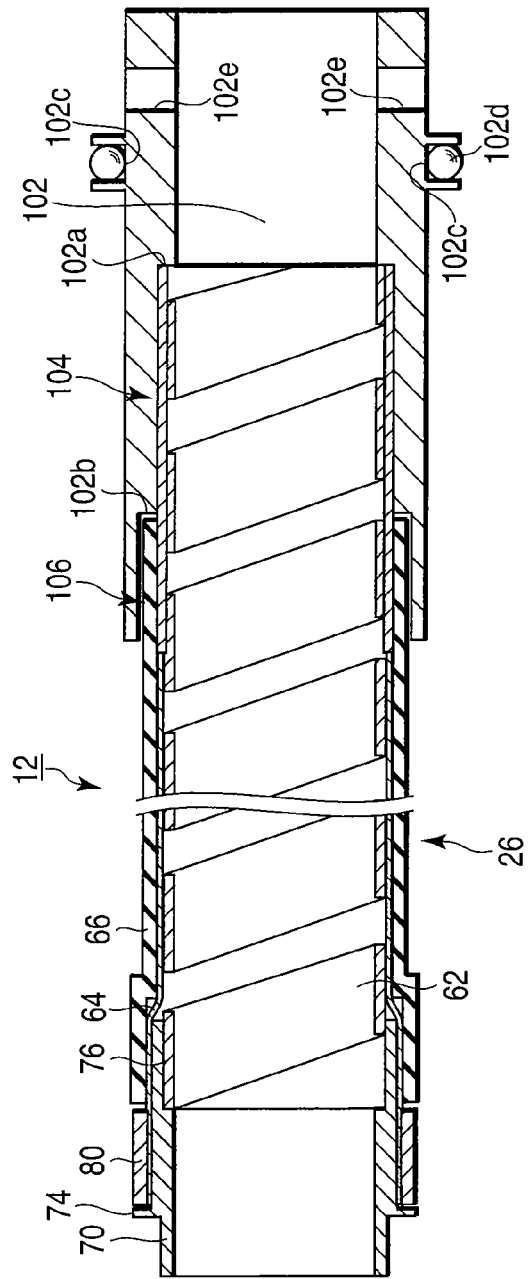
FIGS. 6A and 6B are schematic longitudinal sectional views showing how the connection mouth ring to be connected to the bending portion is disposed at the distal end of the flexible tube of the insertion portion, and an operation portion connection mouth ring to be connected to an operation portion is disposed at the proximal end of the flexible tube of the endoscope according to the first embodiment.
Figure 7:
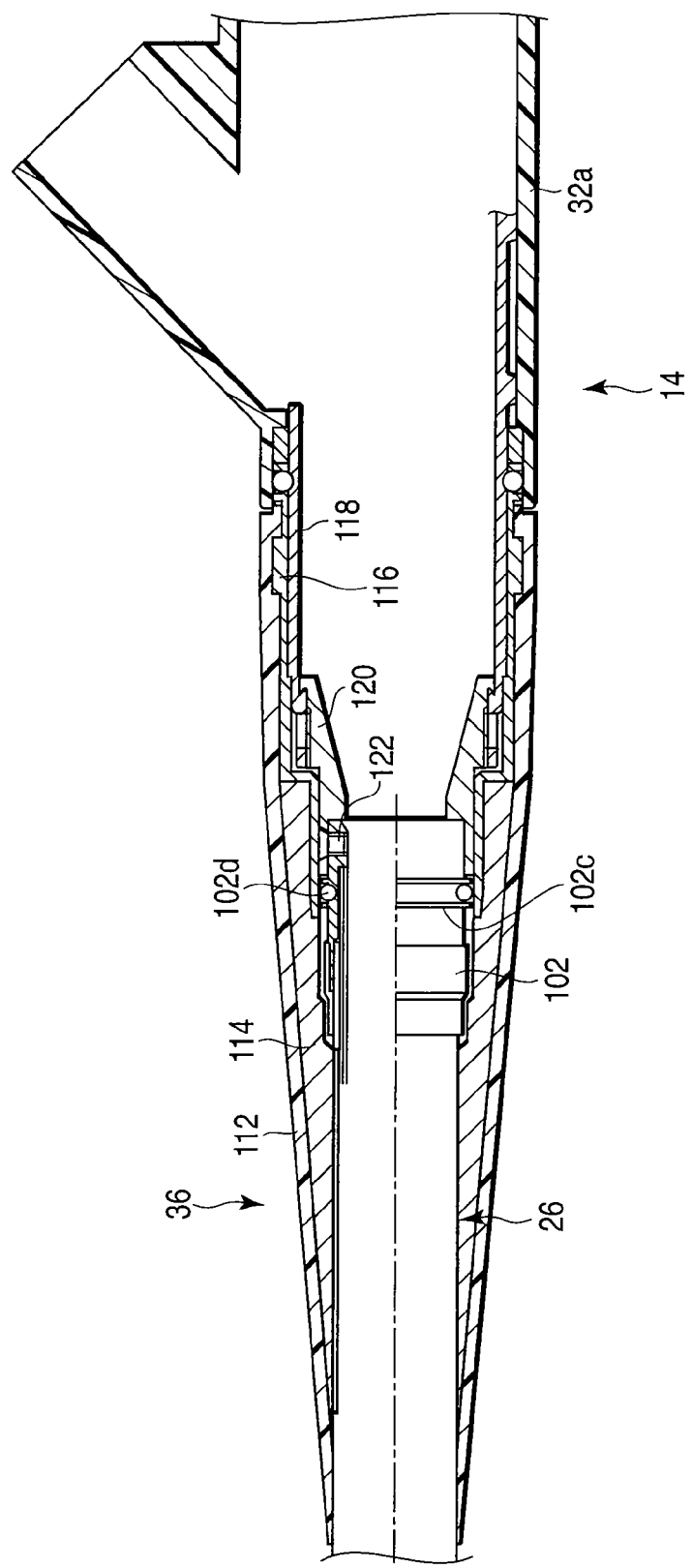
FIG. 7 is a schematic longitudinal sectional view of parts of the insertion portion and the operation portion, showing how the operation portion connection mouth ring at the proximal end of the flexible tube of the insertion portion shown in FIGS. 6A and 6B is disposed in a protection hood of the operation portion.

Next, a structure is illustrated in FIGS. 6A and 7 whereby the flexible tube 26 of the insertion portion 12 of the endoscope 10 is connected to an operation portion connection mouth ring 102 of the operation portion 14.

As shown in FIG. 6A, the operation portion connection mouth ring 102 is substantially cylindrically formed. Inside the operation portion connection mouth ring 102, there are provided a first contact portion 102a with which the proximal end of the helical tube 62 and the proximal end of the braid tube 64 are brought into contact, and a second contact portion 102b with which the proximal end of the outer tube 66 is brought into contact. Since the helical tube 62 and the braid tube 64 are disposed inside the outer tube 66, the inside diameter of the second contact portion 102b is greater than the first contact portion 102a.

Furthermore, a circular-ring-shaped groove 102c is formed in the outer peripheral surface of the operation portion connection mouth ring 102. An O-ring 102d is disposed in the groove 102c. Further, for example, a pair of screw holes 102e is formed on the proximal side of the groove 102c.

A method of connecting the proximal end of the flexible tube 26 to the operation portion connection mouth ring 102 is described below.

The proximal end of the helical tube 62 and the proximal end of the braid tube 64 are, for example, circumferentially brazed together in advance to form a hard portion 104 in which the proximal end of the helical tube 62 and the proximal end of the braid tube 64 are hardened. At this point, the inner peripheral surface of the proximal end of the outer tube 66 is also fixed to the hard portion 104, together with the formation of the hard portion 104. In addition, the proximal end of the outer tube 66 is on the distal side of the flexible tube 26 as compared with the proximal ends of the helical tube 62 and the braid tube 64.

The proximal end of the hard portion 104 is brought into contact with the first contact portion 102a of the operation portion connection mouth ring 102. In this state, the outer peripheral surface of the hard portion 104 is, for example, adhesively bonded or brazed onto the inner peripheral surface of the operation portion connection mouth ring 102. At this point, the proximal end of the outer tube 66 is brought into contact with the second contact portion 102b or disposed slightly closer to the distal side of the flexible tube 26.

Then, the operation portion connection mouth ring 102 disposed at the proximal end of the flexible tube 26 is fixed inside the protection hood 36 of the operation portion 14, as shown in FIG. 7.

The protection hood 36 includes an exterior portion 112, an interior portion 114, and first to third linkage members 116, 118, 120.

The exterior portion 112 is disposed on the outermost side of the protection hood 36. The interior portion 114 is disposed inside the exterior portion 112, and holds the proximal end of the flexible tube 26. The first linkage member 116 is fitted into the exterior portion 112 and the interior portion 114. The second linkage member 118 is screwed to the first linkage member 116, and, although not shown, is also linked to the grip portion 32a. The third linkage member 120 is linked to the second linkage member 118, and is linked by disposing screws 122 in the screw holes 102e of the operation portion connection mouth ring 102.

In addition, the bending portion 24 is not connected to the proximal end of the flexible tube 26 via the connection mouth ring 70 in the example shown in FIG. 6A, but in terms of the order of operation steps, the bending portion 24 may be connected before the operation portion connection mouth ring 102 is connected.

While the proximal end of the flexible tube 26 is connected to the protection hood 36 of the operation portion 14 in the example described here, the protection hood 46 of the universal cable 16 is likewise connected to the operation portion main body 32.

As described above, the following can be said according to this embodiment.

The welded portions α where the helical tube 62 is fixed to the connection mouth ring 70 and the position where the caulking member 80 is caulked against the connection mouth ring 70 are displaced with respect to each other backward and forward along the axis of the connection mouth ring 70. Thus, the part where the braid tube 64 is caulked against the connection mouth ring 70 by the caulking member 80 is disposed at the end of the connection mouth ring 70 opposite to the end to which the helical tube 62 is connected. Therefore, the outside of the welded portions α is not caulked even if the caulking member 80 is caulked against the connection mouth ring 70 after welding has been carried out to connect the connection mouth ring 70 and the helical tube 62 together, so that it is possible to prevent force from being applied directly to the welded portions α. Thus, even if the caulking member 80 is caulked against the connection mouth ring 70, it is possible to effectively prevent disjunction between the connection mouth ring 70 and the helical tube 62. That is, while thermal action (welding) is used to fix the helical tube 62 to the connection mouth ring 70, the caulking member 80 is used to fix the braid tube 64 to the connection mouth ring 70. Moreover, the position where the helical tube 62 is fixed to the connection mouth ring 70 is displaced with respect to the position where the braid tube 64 is fixed to the connection mouth ring 70, such that it is possible to prevent the part where the braid tube 64 is caulked against the connection mouth ring 70 from directly affecting the place where the helical tube 62 is fixed to the connection mouth ring 70. Moreover, the thickness of the connection mouth ring 70 at the position where it is caulked by the caulking member 80 can be greater because the helical tube 62 is not present inside the caulking member 80, so that the caulking member 80 can be firmly caulked against the connection mouth ring 70 to firmly fix the braid tube 64 to the connection mouth ring 70.

At this point, since the width of the caulking member 80 is about 2 mm, and the part where the concave portion 76 of the connection mouth ring 70 overlaps the helical tube is about 1 mm, so that even if these lengths are added together, the length required to fix the helical tube 62 and the braid tube 64 of the flexible tube 26 to the connection mouth ring 70 is only about 3 mm. Thus, the length of the connection mouth ring 70 (the whole length of the hard portion) can be reduced. In this way, a straight tube (connection mouth ring 70) portion between the bending portion 24 and the flexible tube 26 can be reduced to the minimum, thereby allowing higher insertability of the insertion portion 12 into a space achieved by bending the bending portion 24 and the flexible tube 26 than heretofore. Moreover, since fixing each member to the connection mouth ring 70 by caulking and thermal action (welding) permits strength to be obtained with a short range, there is no need for a long joint portion to fix the helical tube 62 and the braid tube 64 to the connection mouth ring 70, so that the hard portion (connection mouth ring 70) can be shorter. That is, it is possible to minimize the length of the hard portion formed at the connection portion between the flexible tube 26 and another tube or the like.

In the medical endoscope 10, improving the bending performance of the bending portion 24 and the flexible tube 26 is especially effective because it can relieve a pain attributed to the insertion into a body cavity or it has a positive effect on a procedure carried out in a situation where a surgical instrument (not shown) is disposed in the insertion portion 12.

Furthermore, the braid tube 64 can be fixed by caulking the caulking member 80 against the connection mouth ring 70. It is thus possible to prevent the outer tube 66 from being damaged by the transmission of heat to the outer tube 66 due to, for example, the welding of the braid tube 64 to the connection mouth ring 70. That is, according to the structure in this embodiment in which the braid tube 64 is fixed to the connection mouth ring 70, the use of heat is not needed for the fixing, so that it is possible to prevent the outer tube 66 from being damaged.

In addition, while the flange portion 74 is used as a positioning portion which projects in the diametrically outward direction of the connection mouth ring 70 to position the caulking member 80 as described in this embodiment, one or more projections (at least one projection) may be formed as the positioning portion for positioning the caulking member 80 instead of the flange portion 74.

In the example (the example in which the bending portion 24 bends in two directions) described in this embodiment, the pair of operation wires 56 is disposed inside the bending tube 52 for the simplification of the drawings and explanation, as shown in FIGS. 2A to 2C. Although not shown, for example, two pairs of operation wires may be disposed inside the bending tube 52. In such a structure, the bending portion 24 can bend in four directions.

While the insertion portion 12 has been described as an example with regard to the connection between the flexible tube 26 and the connection mouth ring 70 in this embodiment, such a structure may also be used between the flexible tube 42 and the connector 44 of the universal cable 16 and between the flexible tube 42 and the operation portion main body 32 of the operation portion 14.

Figure 6B:
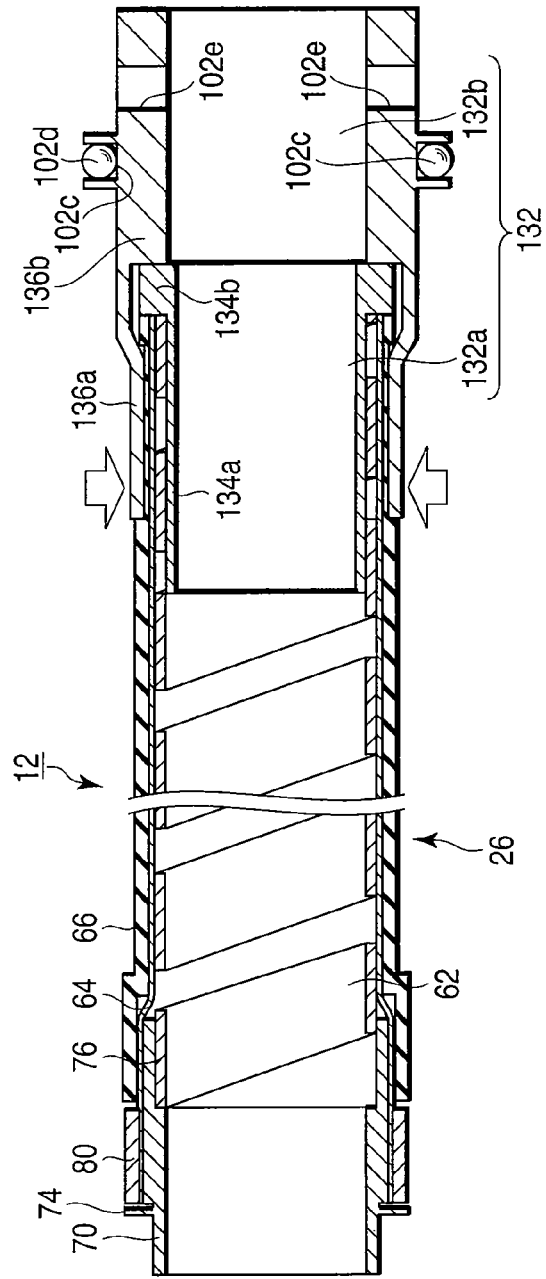

The operation portion main body 32 shown in FIG. 6B may be used instead of the operation portion connection mouth ring 102 shown in FIG. 6A.

As shown in FIG. 6B, an operation portion connection mouth ring 132 includes an inner mouth ring 132a and an outer mouth ring 132b that are substantially cylindrical. The inner mouth ring 132a includes a cylindrical portion 134a and an outward flange portion 134b. The outer mouth ring 132b includes a cylindrical portion 136a and an inward flange portion 136b. The circular-ring-shaped groove 102c is formed in the outer peripheral surface of the inward flange portion 136b of the outer mouth ring 132b. The O-ring 102d is disposed in the groove 102c. Further, for example, a pair of screw holes 102e is formed on the proximal side of the groove 102c.

The outside diameter of the cylindrical portion 134a of the inner mouth ring 132a is formed to be larger than the inside diameter of the proximal end of the helical tube 62 when the helical tube 62 is independent and in a free state (natural state) with no external force applied thereto so that the inner peripheral surface of the helical tube 62 may be in close contact with the outer peripheral surface of the cylindrical portion 134a of the inner mouth ring 132a. The helical tube 62 and the connection mouth ring 70 can be fixed together so that the helical tube 62 is in close contact with the connection mouth ring 70 by the diametrically outward urging force of the helical tube 62 itself. Further, the helical tube 62 is fixed to the cylindrical portion 134a of the inner mouth ring 132a by being laser-welded from the outside of the helical tube 62. At this point, the part where the helical tube 62 overlaps the cylindrical portion 134a of the inner mouth ring 132a can be readily recognized. This ensures that the helical tube 62 and the inner mouth ring 132a can be fixed together.

Furthermore, the helical tube 62, the braid tube 64 and the outer tube 66 are disposed between the outer peripheral surface of the cylindrical portion 134a of the inner mouth ring 132a and the inner peripheral surface of the cylindrical portion 136a of the outer mouth ring 132b. Moreover, the distal end of the cylindrical portion 136a of the outer mouth ring 132b is caulked so that the helical tube 62, the braid tube 64 and the outer tube 66 are held between the cylindrical portion 136a and the outer peripheral surface of the cylindrical portion 134a of the inner mouth ring 132a. That is, the flexible tube 26 is fixed to the operation portion connection mouth ring 132. Such the operation portion connection mouth ring 132 is fixed to the protection hood 36 of the operation portion 14, as shown in FIG. 7.

Second Embodiment

Figure 8:
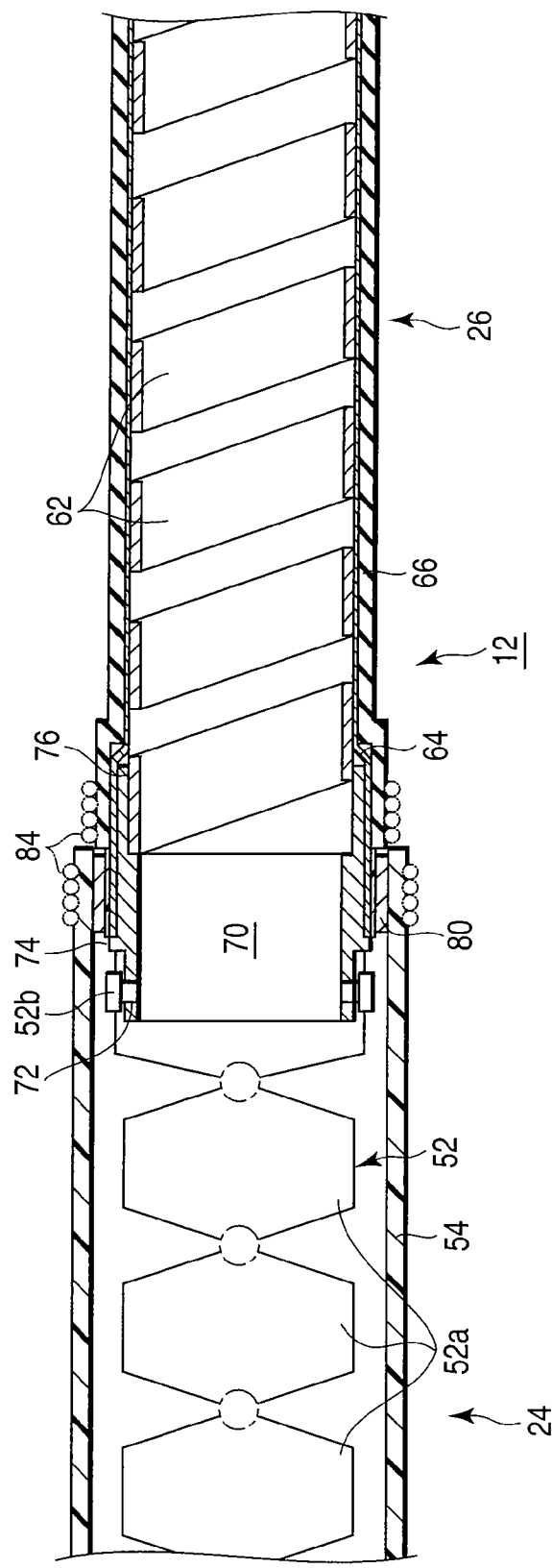
FIG. 8 is a schematic longitudinal sectional view showing a bending portion, a flexible tube and a connection mouth ring for connecting the bending portion to the flexible tube of an insertion portion in the endoscope according to the second embodiment.

Next, a second embodiment is described with FIG. 8. This embodiment is a modification of the first embodiment, and the same signs are assigned to the same members as the members described in the first embodiment, and detailed description is not provided.

As shown in FIG. 8, in the example of this embodiment, not only the distal end of the braid tube 64 described in the first embodiment but also the distal end of the outer tube 66 is caulked against the connection mouth ring 70 by the caulking member 80. At this point, the distal end of the outer tube 66 is previously formed into a small thickness by, for example, polishing so that it is disposed outside the outer tube 66 before the caulking member 80 is caulked.

Masking for the removal of a resin material is typically required during the molding of the outer tube 66, but such masking is not needed, and the outside diameter of a molding core material is constant, so that the outer tube 66 can be more easily molded.

The thickness of a caulking part where the caulking member 80 is caulked can be stable independent of the variation of the outside diameter of the outer tube 66 in resin molding, and the variation of sandwiching strength due to the variation of the thickness of the outer tube 66 can be inhibited.

The outer tube 66 can be disposed inside the caulking member 80, and a cover tube 54 can be disposed outside the caulking member 80, so that watertightness between the bending portion 24 and the flexible tube 26 can be more reliably provided than in the first embodiment.

Third Embodiment

Figure 9:
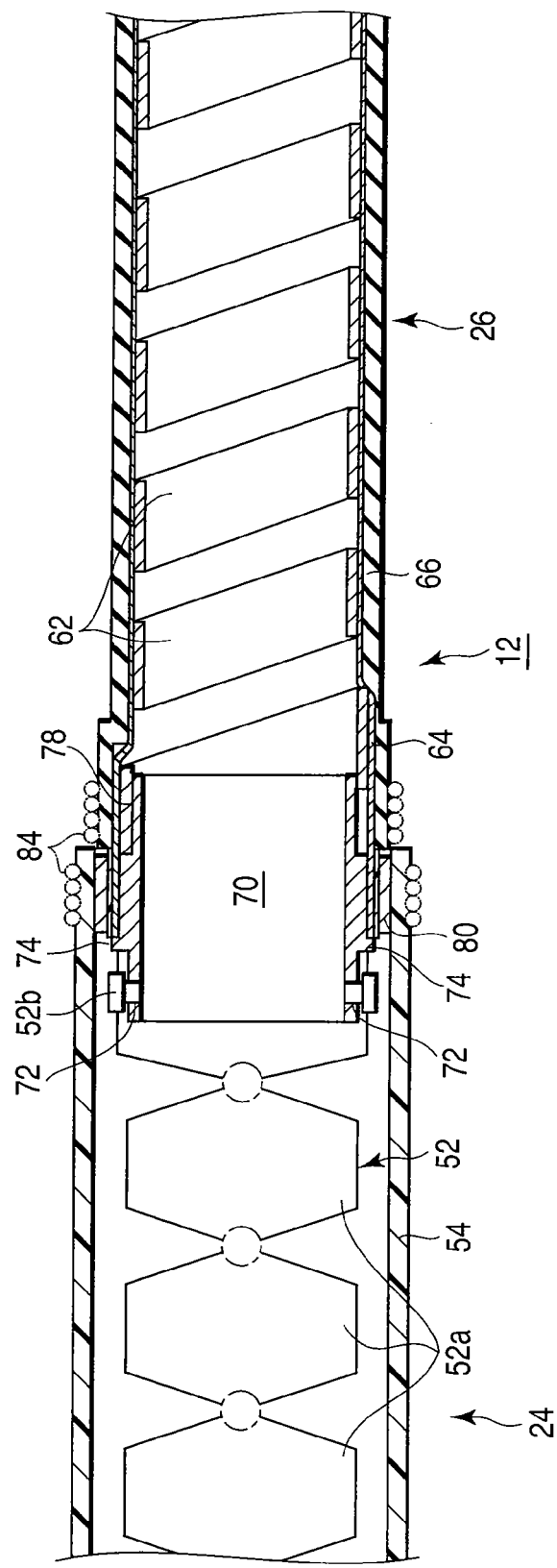
FIG. 9 is a schematic longitudinal sectional view showing a bending portion, a flexible tube and a connection mouth ring for connecting the bending portion to the flexible tube of an insertion portion in the endoscope according to the third embodiment.

Next, a third embodiment is described with FIG. 9. This embodiment is a modification of the first and second embodiments, and the same signs are assigned to the same members as the members described in the first and second embodiments, and detailed description is not provided.

As shown in FIG. 9, in the example of this embodiment, the distal end of the helical tube 62 is disposed outside the proximal end of the connection mouth ring 70, in addition to the structure (see FIG. 8) described in the second embodiment. That is, instead of the concave portion 76 formed on the inner peripheral surface side of the proximal end of the connection mouth ring 70, a concave portion 78 is formed on the outer peripheral surface side.

At this point, the inside diameter of the helical tube 62 when independent and in a free state (natural state) is equal to or smaller than the outside diameter of the concave portion 78 of the connection mouth ring 70 where the helical tube 62 is disposed. Thus, when the distal end of the helical tube 62 is fitted into the concave portion 78 of the connection mouth ring 70, the inner peripheral surface of the distal end of the helical tube 62 can be in close contact with the outer peripheral surface of the concave portion 78 of the connection mouth ring 70. Then, when laser welding is carried out from the outside of the connection mouth ring 70, the part of the distal end of the helical tube 62 that is fitted into the connection mouth ring 70 can be easily known, so that the position to be laser-welded can be visually recognized with ease. Thus, it is possible to more reliably laser-weld the part where the helical tube 62 and the connection mouth ring 70 overlap each other alone.

In addition, while the medical endoscope 10 has been described by way of example in the first to third embodiments, the structures of the flexible tube 26 and the bending portion 24 of the insertion portion 12 and the connection mouth ring 70 can also be used as they are in an industrial endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A manufacturing method of an insertion portion of an endoscope, the insertion portion comprising a flexible tube including a helical tube, a braid tube disposed outside the helical tube, and a flexible outer tube disposed outside the braid tube; and a connection mouth ring connected to an end of the flexible tube and including a concave portion on an inner peripheral surface thereof, the manufacturing method comprising:
    (a) disposing a caulking member outside the helical tube and the braid tube wherein the caulking member is C-shaped and formed of a metal;
    (b) drawing a one end of the helical tube out with respect to a one end of the braid tube;
    (c) bringing the one end of the braid tube into contact with an end of the concave portion of the connection mouth ring, and fitting the helical tube into the connection mouth ring;
    (d) welding the helical tube and the connection mouth ring by thermal action from an outside of the connection mouth ring while the connection mouth ring and the helical tube are in a fitted state;
    (e) pressing the connection mouth ring fixed to the helical tube into the braid tube; and
    (f) plastically deforming the caulking member against the outside of the connection mouth ring by caulking of the caulking member and fixing the braid tube with respect to the connection mouth ring by the caulking of the caulking member, wherein a caulking position of the braid tube and the connection mouth ring is axially away from a welding position of the helical tube and the connection mouth ring.

2. The method according to claim 1, wherein the welding of the helical tube and the connection mouth ring by thermal action is used by laser irradiation from the outside of the connection mouth ring.

3. The method according to claim 1, wherein
    the insertion portion includes an end along an axis thereto, and
    the caulking position of the braid tube and the connection mouth ring is located on a closer side of the end of the insertion portion along the axis than the welding position of the helical tube and the connection mouth ring.

4. The method according to claim 3, wherein
    the caulking member includes an end thereof along the axis;
    the connection mouth ring includes a positioning portion; and
    a position of a side of the end of the caulking member is positioned at the positioning portion of the connection mouth ring.

5. The method according to claim 4, wherein the connection mouth ring includes a flange portion, and
    the method further comprising cutting the one end of the braid tube at a position of the flange portion.

6. The method according to claim 5, wherein the connection mouth ring includes a flange, and
    the method further comprising fixing the one end of the braid tube, the end of the caulking member and the flange portion of the connection mouth ring.

* * * * *